United States Patent
Jang et al.

(10) Patent No.: US 12,226,231 B2
(45) Date of Patent: Feb. 18, 2025

(54) WEARABLE ELECTRONIC DEVICE AND ASSEMBLY METHOD

(71) Applicant: SAMSUNG ELECTRONICS CO., LTD., Suwon-si (KR)

(72) Inventors: Donghoo Jang, Suwon-si (KR); Jonggwan Jung, Suwon-si (KR); Seonho Han, Suwon-si (KR); Yongyi Kim, Suwon-si (KR); Heeyoung Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 472 days.

(21) Appl. No.: 17/589,461

(22) Filed: Jan. 31, 2022

(65) Prior Publication Data

US 2022/0151554 A1    May 19, 2022

Related U.S. Application Data

(63) Continuation of application No. PCT/KR2020/003626, filed on Mar. 17, 2020.

(30) Foreign Application Priority Data

Aug. 1, 2019 (KR) .......................... 10-2019-0093809

(51) Int. Cl.
*A61B 5/282* (2021.01)
*A61B 5/00* (2006.01)
(Continued)

(52) U.S. Cl.
CPC .............. *A61B 5/681* (2013.01); *A61B 5/256* (2021.01); *A61B 5/282* (2021.01); *A61B 5/339* (2021.01);
(Continued)

(58) Field of Classification Search
CPC ........ A61B 2562/164; A61B 2562/166; A61B 2562/185; A61B 5/0015; A61B 5/0059;
(Continued)

(56) References Cited

U.S. PATENT DOCUMENTS

| 9,639,057 B2 | 5/2017 | Jung |
| 10,020,668 B2 | 7/2018 | Adamisin |

(Continued)

FOREIGN PATENT DOCUMENTS

| CN | 105245019 | 1/2016 |
| CN | 107041739 | 8/2017 |

(Continued)

OTHER PUBLICATIONS

Extended Search Report and Written Opinion issued Jul. 18, 2022 in counterpart International Patent Application No. 20847421.3.

(Continued)

*Primary Examiner* — George Manuel
(74) *Attorney, Agent, or Firm* — Nixon & Vanderhye, P.C.

(57) ABSTRACT

An electronic device, according to various example embodiments of the disclosure, may comprise: a display; a processor operatively connected to the display; a cover facing the display and comprising a light transmitting material; a flexible printed circuit board having a first side facing the cover, and a second side corresponding to the opposite side of the first side; a wireless charging coil disposed to surround the flexible printed circuit board; a first bio-signal sensing unit comprising bio-signal sensing circuitry including a light-emitting unit including light-emitting circuitry and a light-receiving unit including light-receiving circuitry mounted on the first side of the flexible printed circuit board; a second bio-signal sensing unit including an internal electrode formed inside the cover, which is a portion facing the (Continued)

flexible printed circuit board, and an external electrode electrically connected to the internal electrode and formed outside the cover; a contact having one end mounted on the first side of the flexible printed circuit board and extending to the cover such that the opposite end thereof is connected to the internal electrode of the second bio-signal sensing unit; and a signal processing unit mounted on the second side of the flexible printed circuit board comprising circuitry configured to process a first bio-signal sensed by the first bio-signal sensing unit and a second bio-signal sensed by the second bio-signal sensing unit.

20 Claims, 12 Drawing Sheets

(51) Int. Cl.
*A61B 5/256* (2021.01)
*A61B 5/339* (2021.01)
*G06F 1/16* (2006.01)
*H02J 50/10* (2016.01)

(52) U.S. Cl.
CPC ............ *A61B 5/7221* (2013.01); *G06F 1/163* (2013.01); *H02J 50/10* (2016.02); *A61B 2562/164* (2013.01); *A61B 2562/166* (2013.01); *A61B 2562/185* (2013.01)

(58) Field of Classification Search
CPC ......... A61B 5/256; A61B 5/282; A61B 5/339; A61B 5/681; A61B 5/7221; G04G 17/04; G04G 17/06; G04G 21/025; G06F 1/163; G06F 1/1635; G06F 1/1658; G06F 1/1684; G06F 1/1698; G06F 1/263; H02J 50/10

See application file for complete search history.

(56) References Cited

U.S. PATENT DOCUMENTS

| | | | |
|---|---|---|---|
| 2015/0102879 | A1 | 4/2015 | Jacobs et al. |
| 2016/0112775 | A1 | 4/2016 | Kim et al. |
| 2017/0000415 | A1 | 1/2017 | Lapetina et al. |
| 2017/0011210 | A1* | 1/2017 | Cheong .................. A61B 5/681 |
| 2017/0093198 | A1 | 3/2017 | Graham et al. |
| 2017/0135593 | A1 | 5/2017 | Huang et al. |
| 2017/0209055 | A1 | 7/2017 | Pantelopoulos et al. |
| 2017/0224236 | A1 | 8/2017 | Ho et al. |
| 2017/0296088 | A1 | 10/2017 | Choi |
| 2018/0039233 | A1* | 2/2018 | Shim ...................... G04G 21/08 |
| 2018/0090975 | A1 | 3/2018 | Lee et al. |
| 2018/0360341 | A1 | 12/2018 | Wang et al. |
| 2018/0365478 | A1 | 12/2018 | Lee et al. |
| 2019/0090806 | A1 | 3/2019 | Clavelle et al. |

FOREIGN PATENT DOCUMENTS

| | | |
|---|---|---|
| CN | 107920742 | 4/2018 |
| CN | 109106342 | 1/2019 |
| CN | 208689385 | 4/2019 |
| EP | 3 017 715 | 5/2016 |
| EP | 3 459 447 | 3/2019 |
| KR | 10-2016-0044811 | 4/2016 |
| KR | 10-2016-0104782 | 9/2016 |
| KR | 10-2017-0038656 | 4/2017 |
| KR | 10-2017-0118439 | 10/2017 |
| KR | 10-2017-0141336 | 12/2017 |
| KR | 10-1931100 | 12/2018 |

OTHER PUBLICATIONS

Chinese Office Action issued May 5, 2023 in corresponding Chinese Patent Application No. 202080055158.2.
Extended Search Report dated Aug. 9, 2024 in European Patent Application No. 24177178.1.
Office Action dated May 27, 2024 in Korean Patent Application No. 10-2019-0093809 and English-language translation.

* cited by examiner

WEARABLE ELECTRONIC DEVICE AND ASSEMBLY METHOD

CROSS-REFERENCE TO RELATED APPLICATIONS

This application is a continuation of International Application No. PCT/KR2020/003626 designating the United States, filed on Mar. 17, 2020, in the Korean Intellectual Property Receiving Office and claiming priority to Korean Patent Application No. 10-2019-0093809, filed on Aug. 1, 2019, in the Korean Intellectual Property Receiving Office, the disclosures of which are incorporated by reference herein in their entireties.

BACKGROUND

Field

The disclosure relates to a wearable electronic device and a method for assembling the same.

Description of Related Art

Wearable electronic devices worn on users' bodies have gradually diversified functions. Moreover, wearable electronic devices have gradually decreased sizes.

In line with increasing interests in good health, wearable electronic devices have been equipped with functions for measuring users' biometric information. Wristwatch-type wearable electronic devices have recently been equipped with various sensors including heartbeat sensors.

Various electronic components enabling electronic devices to perform various functions may be mounted or connected to a printed circuit board (PCB) or flexible printed circuit board (FPCB).

Wearable electronic devices have restrictions on volume due to the wearable characteristics. Various electronic components need to be disposed inside an electronic device in order to equip a wearable electronic device with various functions.

In order to address such limitations, various electronic components need to be disposed inside an electronic device in an efficient manner.

In addition, the contact structure for electric connection between electronic components need to be improved from a planar configuration to a stereoscopic configuration.

SUMMARY

Embodiments of the disclosure may provide an electronic device and an assembly method, wherein relevant components are efficiently disposed inside the electronic device such that the electronic device having a spatial limitation can measure various pieces of biometric information, and electric connection between the components is improved, thereby facilitating assembly.

An electronic device according to various example embodiments of the disclosure may include: a display, a processor operatively connected to the display, a cover facing the display and having at least a portion formed of a light-transmitting material, a flexible printed circuit board having a first surface facing the cover, and a second surface corresponding to an opposite surface of the first surface, a wireless charging coil disposed to surround the flexible printed circuit board, a first bio-signal sensing unit comprising bio-signal sensing circuitry including a light-receiving unit including light-receiving circuitry and a light-emitting unit including light-emitting circuitry mounted on the first surface of the flexible printed circuit board, a second bio-signal sensing unit including an internal electrode formed inside the cover, corresponding to a portion facing the flexible printed circuit board, and an external electrode electrically connected to the internal electrode and formed outside the cover, a contact having one end mounted on the first surface of the flexible printed circuit board, extending to the cover so that the opposite end of the contact is connected to the internal electrode of the second bio-signal sensing unit, and a signal processing unit including signal processing circuitry mounted on the second surface of the flexible printed circuit board configured to process a first bio-signal sensed by the first bio-signal sensing unit and a second bio-signal sensed by the second bio-signal sensing unit.

An assembly method according to various example embodiments of the disclosure may include disposing a wireless charging coil having a ring shape on a cover, and disposing a flexible printed circuit board on the inner circumference of the wireless charging coil, wherein in the disposing of the flexible printed circuit board, a contact is brought into contact with an internal electrode formed on the cover such that the contact extends to the cover with one end of the contact mounted on the flexible printed circuit board.

According to various example embodiments disclosed herein, various components enabling an electronic device to measure various pieces of biometric information are efficiently disposed inside the electronic device such that the limited inner space of the electronic device can be used effectively. In addition, electric connection between the components is improved, thereby facilitating assembly.

BRIEF DESCRIPTION OF THE DRAWINGS

In connection with the description of the drawings, like or similar reference numerals may be used for like or similar elements. Further, the above and other aspects, features and advantages of certain embodiments of the present disclosure will be more apparent from the following detailed description, taken in conjunction with the accompanying drawings, in which.

DETAILED DESCRIPTION

Figure 1:
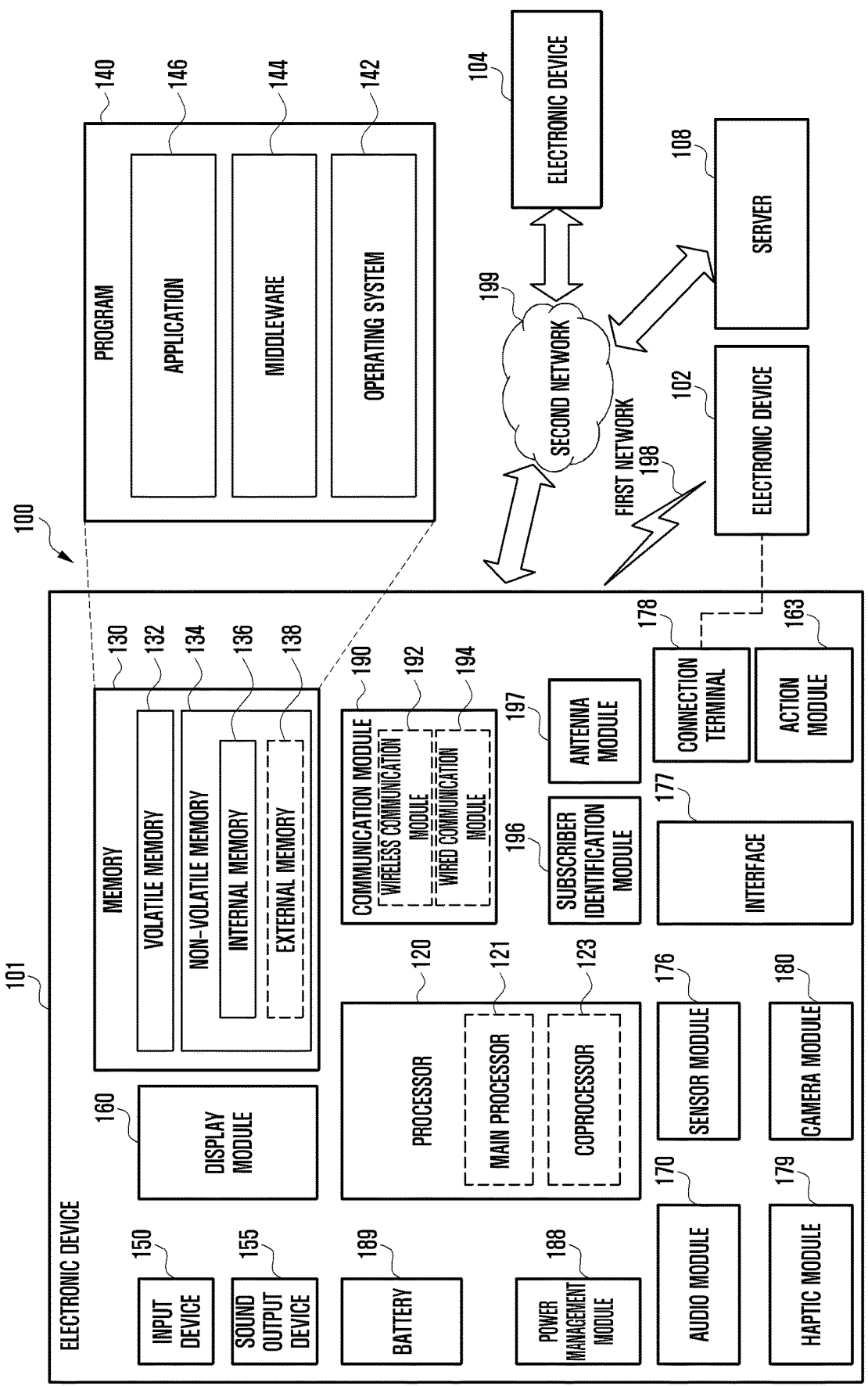
FIG. 1 is a block diagram illustrating an example electronic device in a network environment according to various embodiments.

FIG. 1 is a block diagram illustrating an example electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In various embodiments, at least one (e.g., the display device 160 or the camera module 180) of the components may be omitted from the electronic device 101, or one or more other components may be added in the electronic device 101. In various embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element including a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
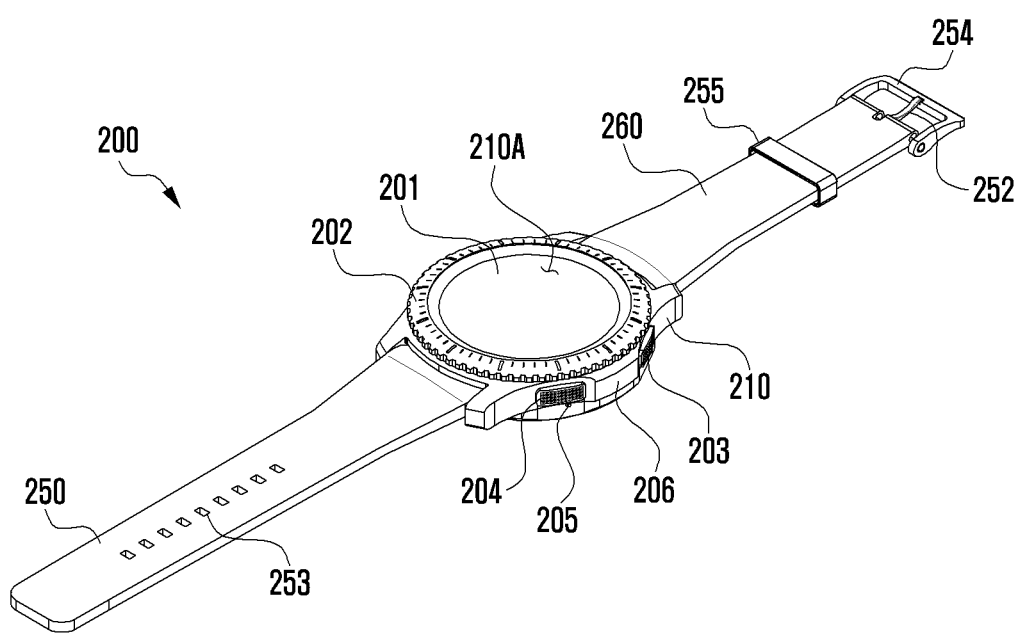
FIG. 2 is a front perspective view of an electronic device according to various embodiments.
Figure 3:
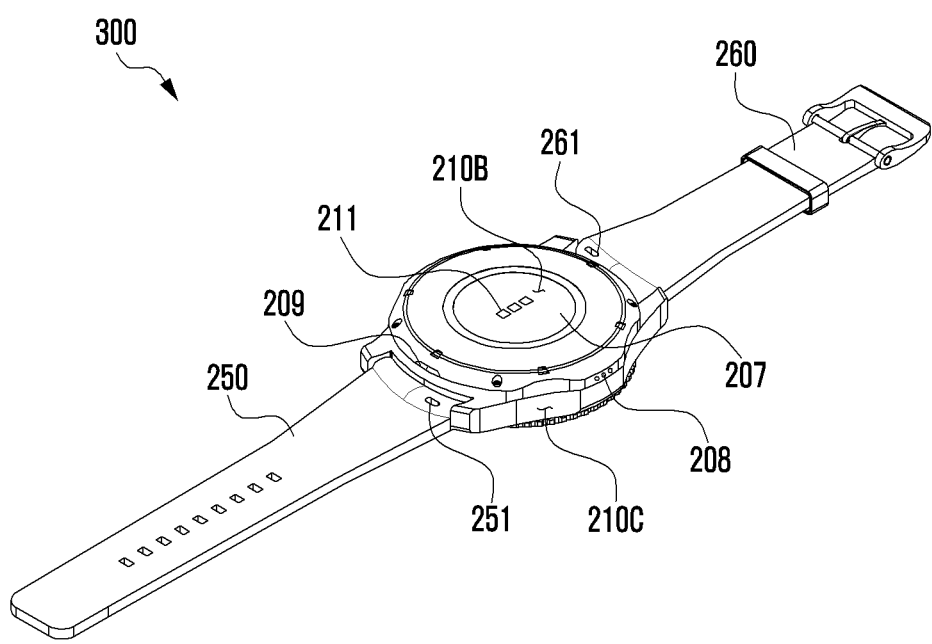
FIG. 3 is a rear perspective view of the electronic device in FIG. 2 according to various embodiments.

Referring to FIG. 2 and FIG. 3, the electronic device 200 according to an embodiment may include a housing 210 including a first surface (or front surface) 210a, a second surface (or rear surface) 210B, and a lateral surface 210C disposed so as to surround a space between the first surface 210a and the second surface 210B, and a coupling member (e.g., band or strap) 250 or 260 connected to at least a portion of the housing 210 and configured to detachably couple the electronic device 200 to a body portion (e.g.: wrist, ankle) of a user. According to an embodiment (not shown), the housing may refer to a structure for configuring a portion of the first surface 210A, the second surface 210B, and the lateral surface 210C in FIG. 2. According to an embodiment, at least a portion of the first surface 210A may be formed of substantially transparent front plate 201 (e.g., glass plate including various coating layers or polymer plate). The second surface 210B may be formed of the substantially opaque rear plate 207. The rear plate 207 may be formed by, for example, coated or colored glass, ceramic, polymers, metals (e.g.: aluminum, stainless steel (STS), or magnesium), or a combination of at least two thereof. The lateral surface 210C may be coupled to the front plate 201 and the rear plate 207 and formed by a lateral bezel structure (or "lateral member") 206 including a metal and/or polymer. In an embodiment, the rear plate 207 and the lateral bezel structure 206 may be integrally formed and include the same material (e.g.: metal material such as aluminum). The coupling member 250 or 260 may be formed of various materials in various shapes. The coupling member may be formed to be integrally and to a plurality of unit links to be movable with each other using a woven fabric, leather, rubber, urethane, metal, ceramic, or a combination of at least two of the materials.

According to an embodiment, the electronic device 200 may include at least one of a display 220 (see FIG. 4), an audio module 205 or 208, a sensor module 211, a key input device 202, 203, or 204, and a connector hole 209. In an embodiment, the electronic device 200 may omit at least one of the components (e.g.: key input device 202, 203, or 204, connector hole 209, or sensor module 211) or additionally include another component.

The display 220 may be visible to outside through, for example, a substantial portion of the front plate 201. The display 220 may have a shape corresponding to the shape of the front plate 201 in various shapes such as a circle, an oval, or a polygon. The display 220 may be combined to or disposed adjacent to a touch sensing circuit, a pressure sensor for measuring a strength (pressure) of a touch, and/or a fingerprint sensor.

The audio module 205 or 208 may include a microphone hole 205 and a speaker hole 208. A microphone for obtaining a sound from outside may be disposed in the microphone hole 205, and in an embodiment, multiple microphones may be arranged to detect a direction of a sound. The speaker hole 208 may be used as a receiver for an outer speaker and phone-calling. In an embodiment, the speaker hole 207 or 214 and the microphone hole 203 may be implemented into one hole and a speaker may be included without a speaker hole 207 or 214 (e.g.: piezo speaker).

The sensor module 211 may generate an electrical signal or a data value corresponding to an internal operation state or external environment state of the electronic device 200. The sensor module 211 may include, for example, a biosensor module 211 (e.g.: HRM sensor) disposed on the second surface 210B of the housing 210. The electronic device 200 may further include at least one sensor module not shown in the drawings, for example, a gesture sensor, a gyro sensor, an air pressure sensor, a magnetic sensor, an acceleration sensor, a grip sensor, a color sensor, an infrared (IR) sensor, a biometric sensor, a temperature sensor, humidity sensor, or an illuminance sensor.

The key input device 202, 203, and 204 may include a wheel key 202 disposed at the first surface 210A of the housing 210 and rotatable in at least one direction, and/or a side button key 202 or 203 disposed at the lateral surface 210C of the housing 210. The wheel key may have a shape corresponding to the front plate 202. In an embodiment, the electronic device 200 may not include a portion or entirety of the key input device 202, 203, and 204 described above, and the excluded key input device 202, 203, and 204 may be implemented as various forms such as a soft key on the display 220. The connector hole 209 may include another connector hole (not shown) capable of receiving a connector (for example, USB connector) for transmitting or receiving power and/or data to or from an external electronic device and a connector for transmitting or receiving an audio signal to or from an external electronic device. The electronic device 200 may further include, for example, a connector cover (not shown) configured to cover a portion of the connector hole 209 and block the ingress of foreign substances to the connector hole.

The coupling member 250 and 260 may be detachably coupled to at least a portion of the housing 210 using a locking member 251 and 261. The coupling member 250 and 260 may include one or more of a fixation member 252, a fixation member fastening hole 253, a band guide member 254, and a band fixation ring 255.

The fixation member 252 may be configured to fix the coupling member 250 and 260 of the housing 210 to a body portion (e.g.: wrist and ankle) of a user. The fixation member fastening hole 253 may fix the coupling member 250 and 260 and the housing 210 to a body portion of a user by counteracting with the fixation member 252. The band guide member 254 is configured to limit the movement range of the fixation member 252 when the fixation member 252 is fastened to the fixation member fastening hole 253 so that the coupling member 250 and 260 is closely coupled to a body portion of a user. The band fixation ring 255 may limit the movement range of the coupling member 250 and 260 in a state in which the fixation member 252 is fastened to the fixation member fastening hole 253.

Figure 4:
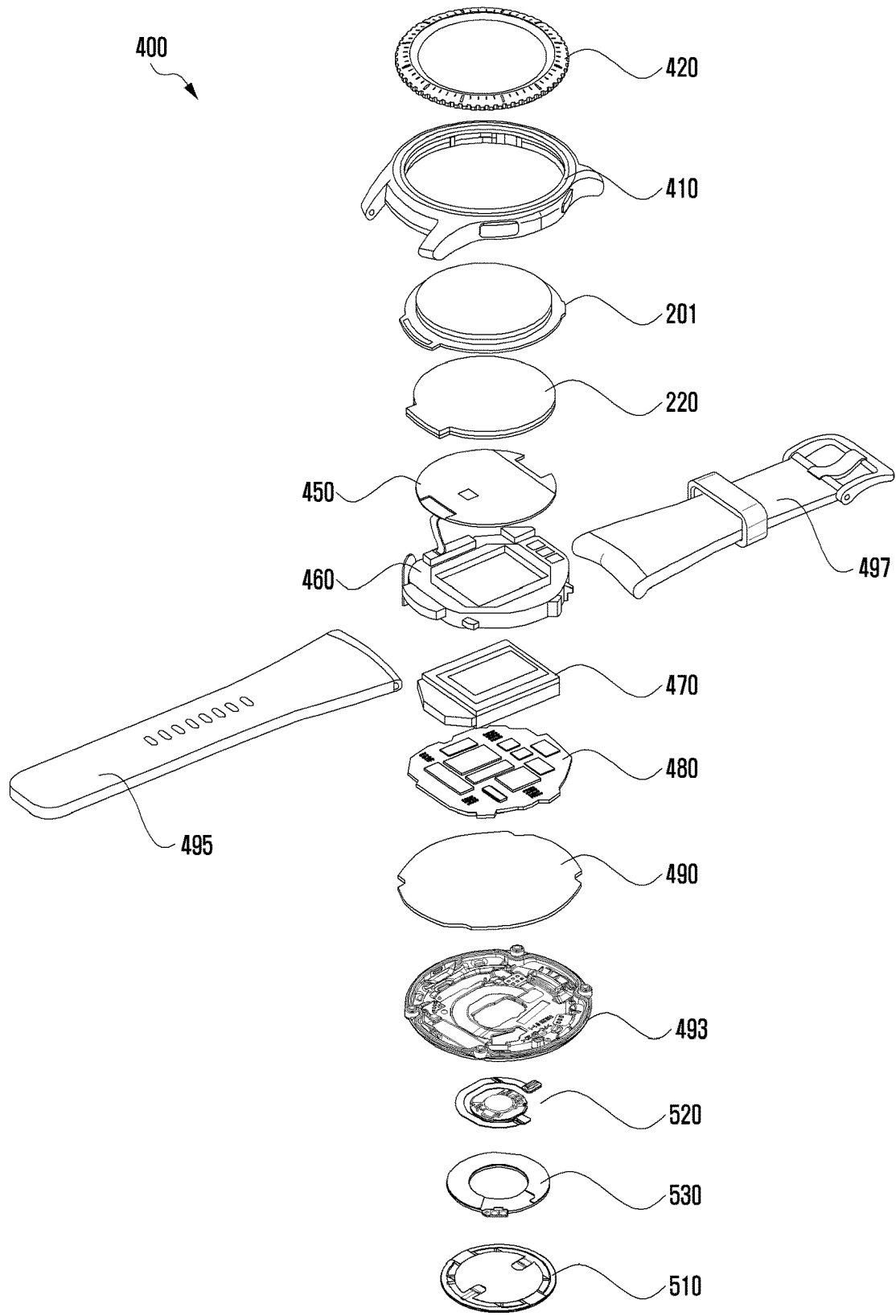
FIG. 4 is an exploded perspective view of the electronic device in FIG. 2 according to various embodiments.

Referring to FIG. 4, the electronic device 400 may include a lateral bezel structure 410, a wheel key 420, a front plate 201, a display 220, a first antenna 450, a second antenna, a support member 460 (e.g., bracket), a battery 470, a printed circuit board 480, a sealing member (e.g., seal) 490, a rear plate 493, and a coupling member (e.g., band or strap) 495 and 497. At least one of the components of the electronic device 400 may be the same as or similar to at least one of the components of the electronic device 200 in FIG. 2 or FIG. 3, and thus the overlapping description thereof will be omitted. The support member 460 may be disposed in the electronic device 400 to be connected to the lateral bezel structure 410 or integrally formed with the lateral bezel structure 410. The support member 460 may be formed of, for example, a metal material and/or a non-metal (e.g.: polymer) material. The support member 460 may have the display 220 coupled to one surface thereof and the printed circuit board 480 coupled to the other surface thereof. A processor, a memory, and/or an interface may be mounted to the printed circuit board 480. The processor may include, for example, one or more of a central processing device, an application processor, a graphic process unit (GPU), an application processor signal processing unit, or a communication processor.

The memory may include, for example, a volatile memory and a nonvolatile memory. The interface may include, for example, a high-definition multimedia interface (HDMI), a universal serial bus (USB) interface, an SD card interface, and/or an audio interface. The interface may electrically or physically connect the electronic device 400 to an external electronic device, and may include, for example, a USB connector, SD card/MMC connector, or an audio connector.

The battery 470 is a device for supplying power to at least one component of the electronic device 400, and may include, for example, a non-rechargeable primary battery, a rechargeable secondary battery, or a fuel cell. At least a part of the battery 470 may be disposed on the substantially same plane as the printed circuit board 480. The battery 470 may be integrally formed to be disposed in the electronic device 200 or may be disposed to be attachable to/detachable from the electronic device 200.

The first antenna 450 may be disposed between the display 220 and the support member 460. The first antenna 450 may include, for example, a near field communication (NFC) antenna, a wireless charging antenna, and/or a magnetic secure transmission (MST) antenna. The first antenna 450, for example, may perform a near field communication with an external electronic device, wirelessly transmit and receive power required for charging, or transmit a magnetism-based signal including a near field communication signal or payment data. In an embodiment, an antenna structure may be formed of a part or a combination of the lateral bezel structure 410 and/or the support member 460.

The second antenna 455 may be disposed between the printed circuit board 480 and the rear plate 493. The second antenna 455 may include, for example, a near field communication (NFC) antenna, a wireless charging antenna, and/or a magnetic secure transmission (MST) antenna. The second antenna 455, for example, may perform a near field communication with an external electronic device, wirelessly transmit and receive power required for charging, or transmit a magnetism-based signal including a near field communication signal or payment data. In an embodiment, an antenna structure may be formed of a part or a combination of the lateral bezel structure 410 and/or the rear plate 493.

The sealing member 490 may include a seal and be disposed between the lateral bezel structure 410 and the rear plate 493. The sealing member 490 may be configured to block moisture and foreign substances from being introduced from the outside to a space surrounded by the lateral bezel structure 410 and the rear plate 493.

Figure 5:
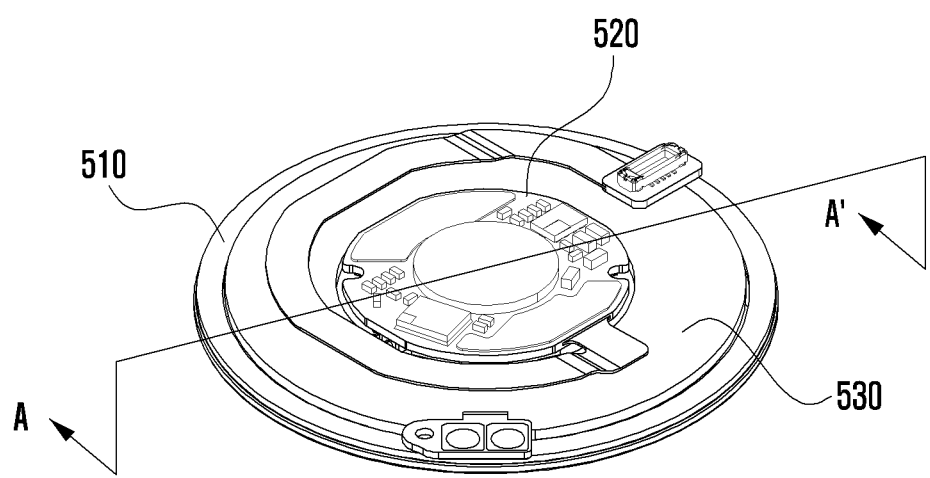
FIG. 5 is a perspective view of a combined state of a flexible printed circuit board, a wireless charging coil, and a cover according to various embodiments.
Figure 6A:
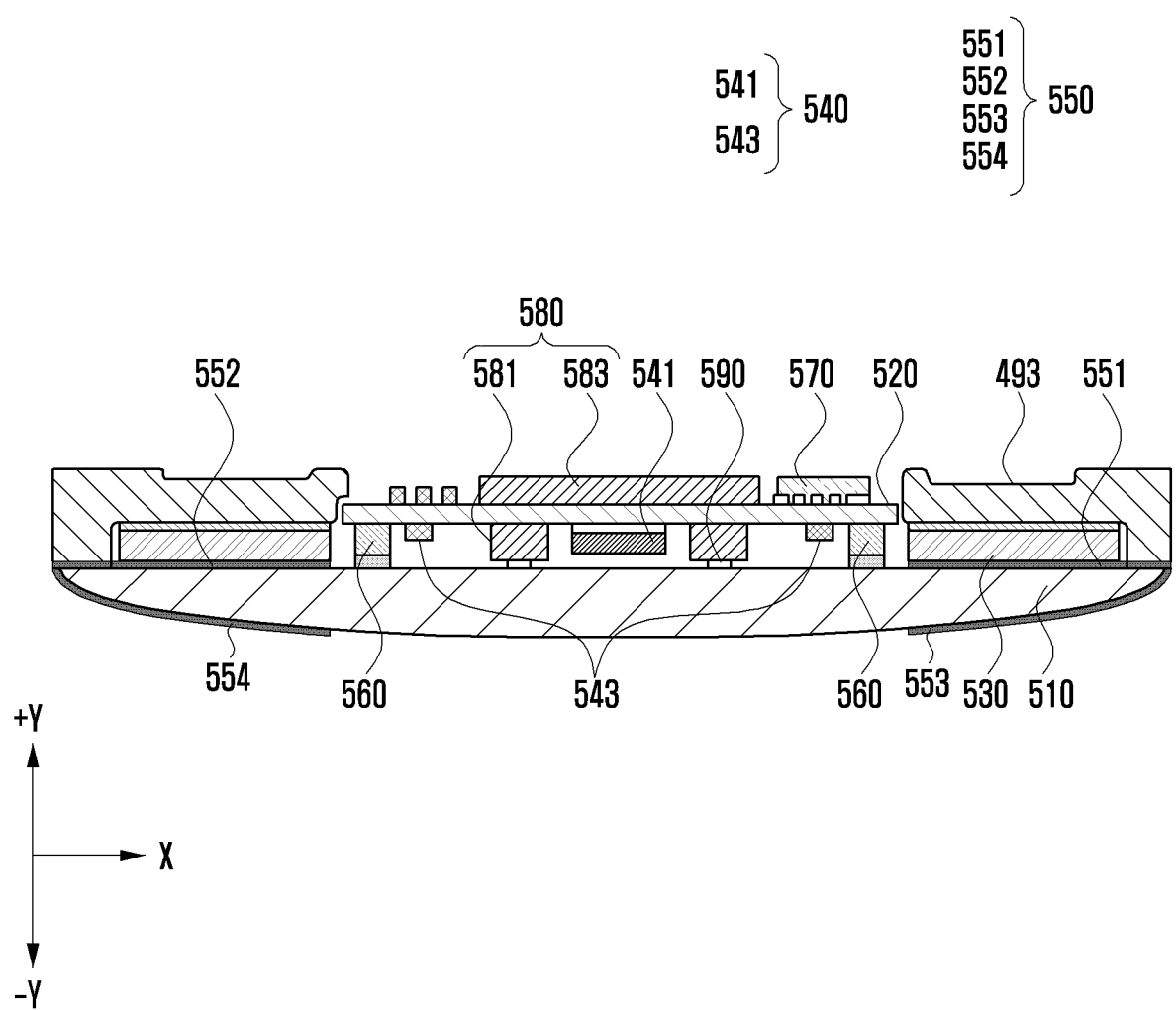
FIG. 6A and FIG. 6B are cross-sectional views of FIG. 5, taken along line A-A according to various embodiments.
Figure 6B:
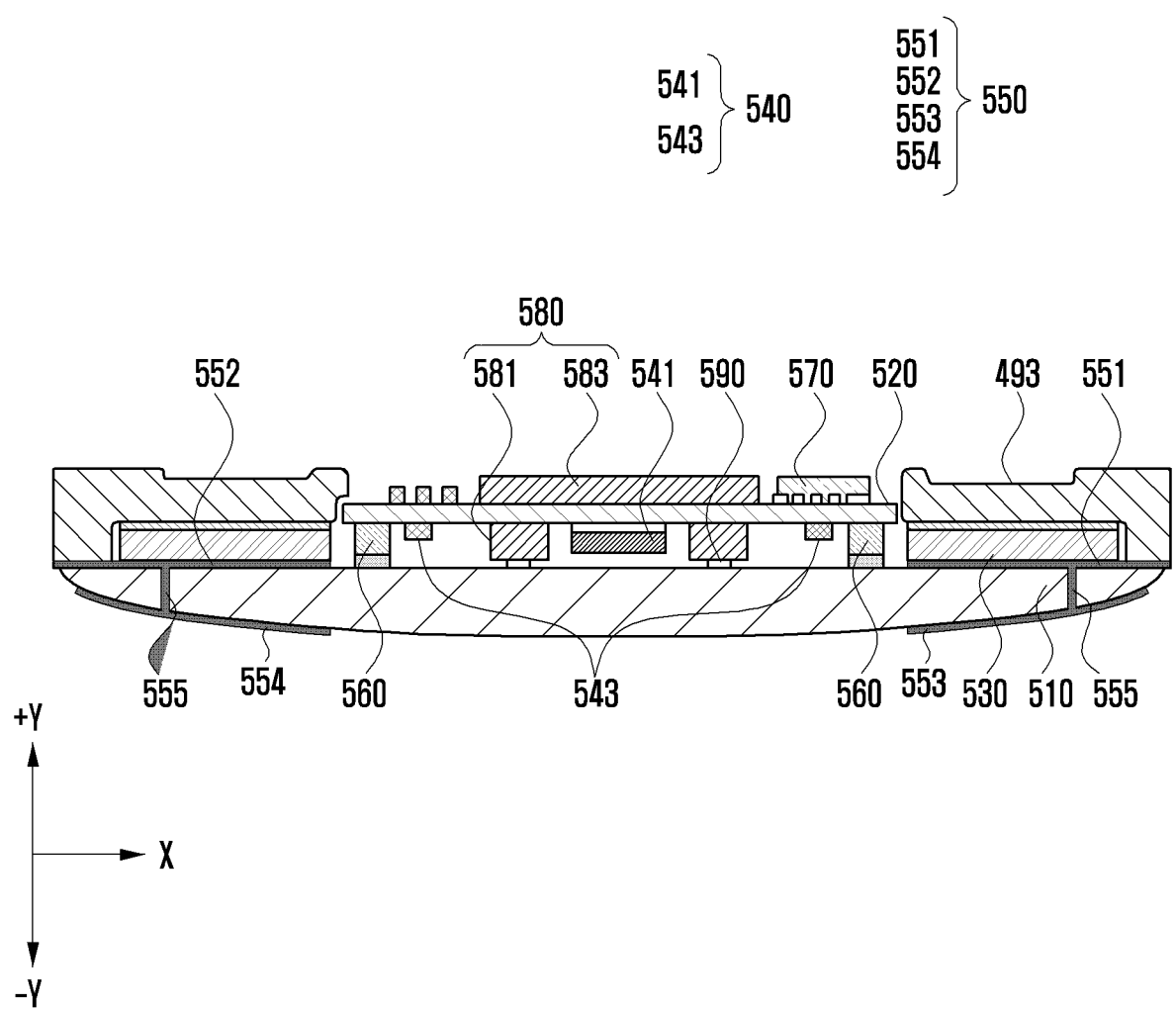
Figure 7A:
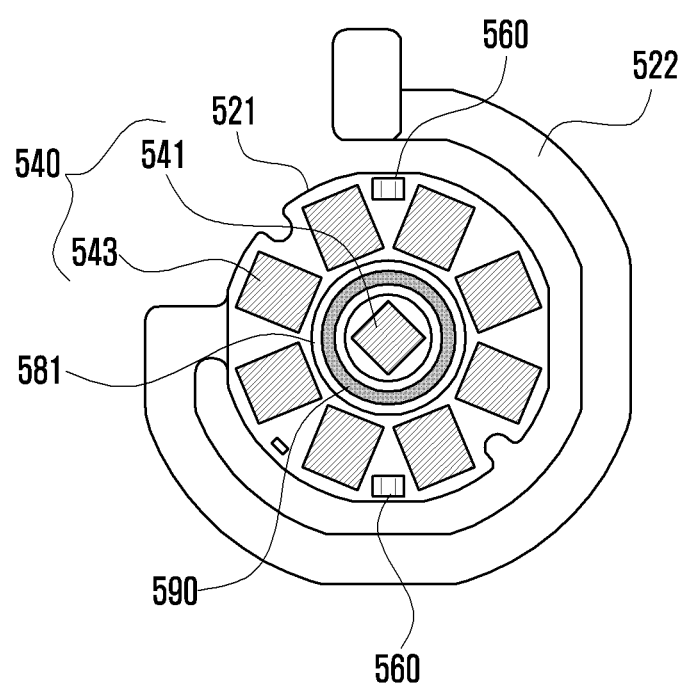
FIG. 7A is a diagram illustrating a plan view the flexible printed circuit board illustrated in FIG. 5 according to various embodiments.
Figure 7B:
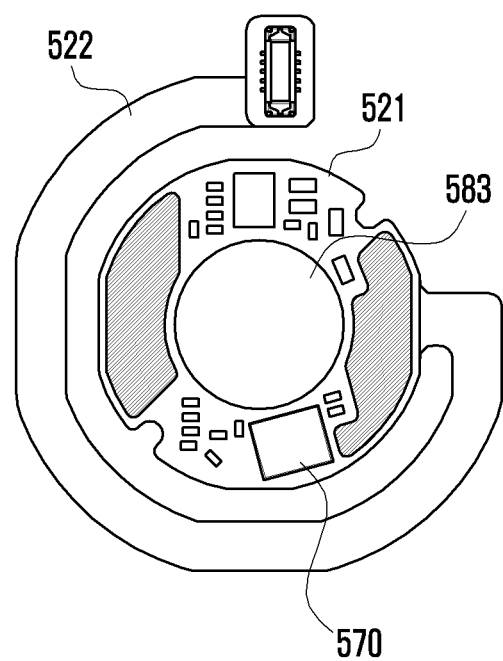
FIG. 7B is a diagram illustrating a rear view of the flexible printed circuit board illustrated in FIG. 5 according to various embodiments.

FIG. 5 is a perspective view of a combined state of a flexible printed circuit board 520, a wireless charging coil 530, and a cover 510 according to various embodiments, FIG. 6A and FIG. 6B are cross-sectional views of FIG. 5, taken along line A-A according to various embodiments, FIG. 7A is a diagram illustrating a plan view of the flexible printed circuit board 520 illustrated in FIG. 5 according to various embodiments, and FIG. 7B is a diagram illustrating rear view of the flexible printed circuit board 520 illustrated in FIG. 5 according to various embodiments.

An electronic device (e.g., electronic device in FIG. 1 or electronic device in FIG. 2 to FIG. 4) according to various embodiments of the disclosure may include a display (e.g., display device 160 in FIG. 1 or display 220 in FIG. 4), a processor (e.g., processor 120 in FIG. 1), a cover 510 (e.g., rear plate 493 in FIG. 4), a flexible printed circuit board 520, a wireless charging coil 530 (e.g., second antenna 455 in FIG. 4), a first bio-signal sensing unit (e.g., including bio-signal sensing circuitry) 540, a second bio-signal sensing unit (e.g., including bio-signal sensing circuitry) 550, a contact unit (e.g., a contact) 560, a signal processing unit (e.g., including processing circuitry) 570, and a magnetic member (e.g., including magnets 581, 583) 580. The first bio-signal sensing unit 540, the contact unit 560, and the signal processing unit 570 mounted to the flexible printed circuit board 520 and the second bio-signal sensing unit 550 mounted to the cover 510 may comprise a sensor module (e.g., sensor module 211 in FIG. 3).

The display may deliver information to a user. The display of the electronic device according to various embodiments disclosed herein may be a display device in FIG. 1 or a display in FIG. 4. The description of the display will be replaced with the description of the display device in FIG. 1 and the display in FIG. 4 above.

The cover 510 may be disposed at a position facing the display in the electronic device. When the direction in which the display displays information on the electronic device is referred to as the front surface of the electronic device, the cover 510 may be disposed on the rear surface of the electronic device. As shown in FIG. 6A and FIG. 6B, the cover 510 may have a convex shape. When the surface facing the flexible printed circuit board 520 is referred to as an inner side of the cover 510 and the opposite side as an outer side of the cover 510, the outer side of the cover 510 may be formed to be convex. When the electronic device according to various embodiments disclosed herein is an electronic device mounted on a wrist, the outer side of the cover may be in contact with a wrist of a user. At least a portion of the cover 510 may be formed of a light-transmitting material. In some cases, the cover 510 may be formed of a material such as glass or a transparent resin through which light may penetrate.

Referring to FIG. 7A and FIG. 7B, the flexible printed circuit board 520 may include a substrate body 521 to which various electronic components are mounted, and a substrate connector 522 configured to electrically connect the flexible printed circuit board 520 to a printed circuit board (e.g., printed circuit board 480 in FIG. 4). The flexible printed circuit board 520 may include a first surface facing the cover 510 and a second surface corresponding to the opposite surface of the first surface. The flexible printed circuit board 520 may be formed of a flexible material, thereby being bendable. The substrate connector 522 may be connected to the substrate body 521 at one end thereof and connected to the printed circuit board (e.g.: printed circuit board 480 in FIG. 4) via the wireless charging coil 530 disposed so as to surround the flexible printed circuit board 520. The substrate connector 522 may be in a bent state due to a step between the flexible printed circuit board 520 and the wireless charging coil 530. As described above, the flexible printed circuit board 520 is formed of a flexible material and thus the substrate connector 522 may electrically connect the flexible printed circuit board 520 to the printed circuit board (e.g., printed circuit board 480 in FIG. 4) even in a bent state.

The wireless charging coil 530 may disposed to surround the flexible printed circuit board 520. Referring to FIG. 5 to FIG. 6A and FIG. 6B, the wireless charging coil 530 may have a ring shape in which a wire including a metal material is wound. The flexible printed circuit board 520 may be disposed at the center of the ring-shaped wireless charging coil 530. The wireless charging coil 530 may provide and receive a power through an external charging device. The wireless charging coil 530 may be electrically connected to the printed circuit board (e.g.: printed circuit board 480 in FIG. 4) to transmit a power of an external charging device to the printed circuit board (e.g.: printed circuit board 480 in FIG. 4).

The first bio-signal sensing unit 540 may include various bio-signal sensing circuitry and sense a first bio-signal and include a light-emitting unit 541 and a light-receiving unit 543.

Referring to FIG. 6A, FIG. 6B, and FIG. 7A, the light-emitting unit 541 may include various light-emitting circuitry and be mounted on the first surface of the flexible printed circuit board 520. The light-emitting unit 541 may include a light-emitting element such as a light-emitting diode (LED) and/or an organic light-emitting diode (OLED). In addition thereto, the light-emitting unit 541 may include various light-emitting elements.

The light-receiving unit 543 may include various light-receiving circuitry and be mounted on the first surface of the flexible printed circuit board 520. As shown in FIG. 7A, the multiple light-receiving units 543 may be arranged around the light-emitting unit 541 in a circular shape. The light-receiving unit 543 may be a light-receiving element for converting an optical energy to an electric energy. Examples of such a light-receiving element may include a photo diode.

The first bio-signal sensed by the first bio-signal sensing unit 540 may include a bio-signal related to a cardiac impulse of a user. Hereinafter, an operation of sensing the first bio-signal by the first bio-signal sensing unit 540 including the light-emitting unit 541 and the light-receiving unit 543 will be described in brief.

The first bio-signal sensing unit 540 may use a difference in optical response caused by oxygen saturation of hemoglobin in blood. The light provided by the light-emitting unit 541 may be transferred to a user body through the cover 510. The light-receiving unit 543 receives reflected light of the light transferred to the user body. The reflected light received by the light-receiving unit 543 has a periodicity due to the difference in optical response caused by oxygen saturation of hemoglobin in blood. The first bio-signal sensing unit 540 may sense a bio-signal related to a cardiac impulse of a user using the periodicity. In some cases, the bio-signal related to a cardiac impulse of a user may be more accurately processed using movement information obtained by indirectly sensing a user movement through a sensor (e.g.: acceleration sensor, gyro sensor) for sensing the position of the electronic device. The signal processing unit 570 may control or process the operation of the first bio-signal sensing unit 540, the first bio-signal sensed thereby, and the like. In some cases, a processor (e.g.: processor 120 in FIG. 1) of the electronic device may operate the first bio-signal sensing unit 540 and process the first bio-signal sensed by the first bio-signal sensing unit 540. The signal processing unit 570 and the processor (e.g.: processor 120 in FIG. 1) of the electronic device may divide and process the instructions required for process of a signal and control.

The sensing of the first bio-signal of the first bio-signal sensing unit 540 described above explains the representative principle of obtaining cardiac impulse-related information using the light-emitting unit 541 and the light-receiving unit 543, and the first bio-signal sensing unit 540 according to various embodiments disclosed herein may obtain cardiac impulse-related information as the first bio-signal using various other methods in addition thereto.

The second bio-signal sensing unit 550 may include various bio-signal sensing circuitry and sense a second bio-signal and include an internal electrode 551 and 552 and an external electrode 553 and 554.

The internal electrode 551 and 552 may include a conductive material and may be disposed inside the cover 510 as shown in FIG. 6A and FIG. 6B. As described above, the inside of the cover 510 may refer to a direction in which the cover 510 and the flexible printed circuit board 520 face to each other. Therefore, the inner surface of the cover 510 is a surface of the cover 510, facing the flexible printed circuit board 520. The internal electrode 551 and 552 may include a first internal electrode 551 and a second internal electrode 552. The first internal electrode 551 and the second internal electrode 552 may be formed on the inner surface of the cover 510. The first internal electrode 551 and the second internal electrode 552 may be in contact with the contact unit 560 to be described below. As shown in FIG. 6A and FIG. 6B, a cross-sectional area of the cover 510 may be larger than that of the flexible printed circuit board 520 on which the contact unit 560 is mounted. The first internal electrode 551 and the second internal electrode 552 may extend from the outer circumference of the cover 510 to the center of the cover 510 to come in contact with the contact unit 560.

The external electrode 553 and 554 may include a conductive material and may be disposed outside the cover 510 as shown in FIG. 6A and FIG. 6B. The outer surface of the cover 510 corresponds to a surface opposite to the inner surface of the cover 510 described above. As described above, the outer surface of the cover 510 is the surface in contact with the body of a user. Therefore, the outer surface of the cover 510 may be in contact with the body of a user. The external electrode 553 and 554 disposed on the outer surface of the cover 510 may be in contact with the body of a user. The external electrode 553 and 554 may include a first external electrode 553 and a second external electrode 554. The first external electrode 553 may be electrically connected to the first internal electrode 551 of the internal electrode 551 and 552. The second external electrode 554 may be electrically connected to the second internal electrode 552 of the internal electrode 551 and 552. As shown in FIG. 6A, through the outer circumferential portion of the cover 510, the first external electrode 553 may be connected to the first internal electrode 551 and the second external electrode 554 may be connected to the second internal electrode 552. A method for connecting the external electrode 553 and 554 and the internal electrode 551 and 552 may be variously implemented. For example, as shown in FIG. 6B, the external electrode 553 and 554 and the internal electrode 551 and 552 may be connected to each other through a passage 555 formed inside the cover 510. A conductor may be inserted so as to electrically connect the external electrode 553 and 554 to the internal electrode 551 and 552 respectively through the passage 555. According to various embodiments, the passages may have a through-hole shape.

The second bio-signal sensed by the second bio-signal sensing unit 550 may include a bio-signal related to an electrocardiogram of a user. Hereinafter, an operation of sensing the second bio-signal by the second bio-signal sensing unit 550 including the external electrode 553 and 554 and the internal electrode 551 and 552 will be described in brief.

The second bio-signal sensing unit 550 may sense an electrocardiogram-related signal by sensing an electrical signal upon myocardial contraction. When the myocardium contacts or relaxes, an action potential spreads from the heart throughout the body. When electrodes are attached to various parts of the body, the potential difference generated by the current caused by the contraction or relaxation of the myocardium can be obtained. For example, such a potential difference may be obtained using the first external electrode 553 of the second bio-signal sensing unit 550 and an electrocardiogram electrode of an external electronic device. When the electronic device according to various embodiments disclosed herein is an electronic device mounted on a wrist, the first external electrode 553 may be in contact with a wrist of a user. In this case, by contacting the electrocardiogram electrode of an external electronic device with an opposite finger or wrist, the potential difference between opposite wrists caused by a cardiac impulse may be obtained. The second external electrode 554 may function as a ground electrode. A voltage change over time may be sensed in the form of a waveform by the external electrode 553 and the electrocardiogram electrode of an external electronic device. The second bio-signal associated with electrocardiogram may be sensed by analyzing a shape (amplitude, period, kurtosis, and the like) of the waveform. The signal processing unit 570 may include various signal processing circuitry and control or process the operation of the second bio-signal sensing unit 550, the second bio-signal sensed thereby, and the like. In some cases, a processor (e.g.: processor 120 in FIG. 1) of the electronic device may operate the second bio-signal sensing unit 550 and process the second bio-signal sensed by the second bio-signal sensing unit 550. The signal processing unit 570 and the processor (e.g.: processor 120 in FIG. 1) of the electronic device may divide and process the instructions required for process of a signal and control.

The sensing of the second bio-signal of the second bio-signal sensing unit 550 described above explains the representative principle of obtaining electrocardiogram-related information using multiple electrodes, and the second bio-signal sensing unit 550 according to various embodiments disclosed herein may obtain the electrocardiogram-related information as the second bio-signal using various other methods in addition thereto.

Referring to FIG. 6A and FIG. 6B, one end of the contact unit 560 may be mounted on the first surface of the flexible printed circuit board 520. The other end of the contact unit 560 may be in contact with the internal electrode 551 and 552 of the second bio-signal sensing unit 550. The contact unit 560 may include a conductive material. The contact unit 560 may be connected to the internal electrode 551 and 552 of the second bio-signal sensing unit 550 so as to electrically connect the internal electrode 551 and 552 to the flexible printed circuit board 520. To this end, the contact unit 560 may extend in a direction perpendicular to the first surface of the flexible printed circuit board 520. With reference to FIG. 6A and FIG. 6B, the contact unit 560 may extend in −Y direction. As such, the contact unit 560 is formed to extrude toward the first surface of the flexible printed circuit board 520, and thus the internal electrode 551 and 552 may be electrically connected to the flexible printed circuit board 520 in a simple manner Two contact units 560 may be provided to be electrically connected to the first internal electrode 551 and the second internal electrode 552 of the internal electrode 551 and 552, respectively.

The inside of the contact unit 560 may be filled with a buffer substance. Referring to FIG. 6A and FIG. 6B, the contact unit 560 may support the center portion of the cover 510. The buffer substance filled inside the contact unit 560 may buffer an external force applied to the center portion of the cover 510. Although the inside of the contact unit 560 is not filled with the buffer substance, the contact unit 560 has a pre-configured elasticity and thus may buffer an external force applied to the center portion of the cover 510.

The signal processing unit 570 may include various signal processing circuitry and process the first bio-signal sensed by the first bio-signal sensing unit 540 and the second bio-signal sensed by the second bio-signal sensing unit 550. For example, the signal processing unit 570 may convert the first bio-signal and the second bio-signal in an analogue signal form into signals in a digital form or amplify the first bio-signal and the second bio-signal. Referring to FIG. 6A, FIG. 6B, and FIG. 7A, the signal processing unit 570 may be mounted on the second surface of the flexible printed circuit board 520. As such, the flexible printed circuit board 520 having a small area may be efficiently utilized using both surfaces of the flexible printed circuit board 520.

The magnet member 580 may include a first magnet 581 and a second magnet 582. Referring to FIG. 6A, FIG. 6B, and FIG. 7A, the first magnet 581 may be disposed on the first surface of the flexible printed circuit board 520. The first magnet 581 may be formed in a ring shape and disposed at the center of the first surface of the flexible printed circuit board 520. The light-emitting unit 541 of the first bio-signal sensing unit 540 described above may be disposed inside the first magnet 581. The light-receiving unit 543 of the first bio-signal sensing unit 540 may be arranged along the outer circumference of the first magnet 581.

Referring to FIG. 6A, FIG. 6B, and FIG. 7A, the second magnet 583 may be disposed on the second surface of the flexible printed circuit board 520. The space in which the second magnet 583 is disposed may be a space formed by the signal processing unit 570 mounted on the second surface of the flexible printed circuit board 520. Referring FIG. 6A and FIG. 6B, the volume of the signal processing unit 570 itself may form a space corresponding to the height of the signal processing unit 570 between the flexible printed circuit board 520 and a component in contact with the flexible printed circuit board 520. The second magnet 583 may be disposed in this space. The central axis of the first magnet 581 may be aligned with the central axis of the second magnet 583.

The first magnet 581 and the second magnet 583 may fix and connect the electronic device according to various embodiments disclosed herein to a charging device. As describe above, the electronic device may include a wireless charging coil 530. When the wireless charging coil 530 of the electronic device is disposed within a configured range in relation to a charging coil of a charging device, the electronic device may be charged wirelessly by the charging device. The charging device may include a magnet therein. The relative positions of the first magnet 581 and the second magnet 583, and the wireless charging coil 530 in the electronic device are determined. Likewise, the relative positions of the magnet of the charging device and the charging coil of the charging device are determined. When the magnet inside the charging device and the first magnet 581 and the second magnet 583 attract each other, the charging coil of the charging device and the wireless charging coil 530 of the electronic device are arranged at positions to correspond to each other, and then charging is performed. In this way, the first magnet 581 and the second magnet 583 may provide mounting conformability so as to cause the electronic device to be disposed at a position at which the wireless charging may be performed.

In addition, the attraction between the first magnet 581 and the second magnet 583 and the magnet of the charging device may provide mounting force by which the electronic device and the charging device are fixed to each other while charging is performed.

In order to ensure the mounting conformability and mounting force by a magnet, the volume of the magnet needs to be a certain level or more. The electronic device according to various embodiments disclosed herein may ensure sufficient mounting conformability and mounting force through the first magnet 581 and the second magnet 583 disposed on opposite surfaces of the flexible printed circuit board 520. Specifically, as described above, the second magnet 583 is disposed in a space formed by the signal processing unit 570, and thus the electronic device may minimize and/or reduce the space receiving the first magnet 581 and the second magnet 583.

An optical shielding member (e.g., shield) 590 may optically shield between the first magnet 581 and the cover 510. As describe above, the light-emitting unit 541 of the first bio-signal sensing unit 540 may be disposed at the center of the first magnet 581. In order for the first bio-signal sensing unit 540 to sense an accurate first bio-signal, the light generated from the light-emitting unit 541 should not leak between the first magnet 581 and the cover 510. This is because the light-receiving unit 543 needs to receive only the light reflected from the body of a user. The optically shielding member 590 may be installed on one of the first magnet 581 and the cover 510 between the first magnet 581 and the cover 510 to shield between the first magnet 581 and the cover 510 such that the light-emitting unit 541 is optically shielded.

Figure 8:
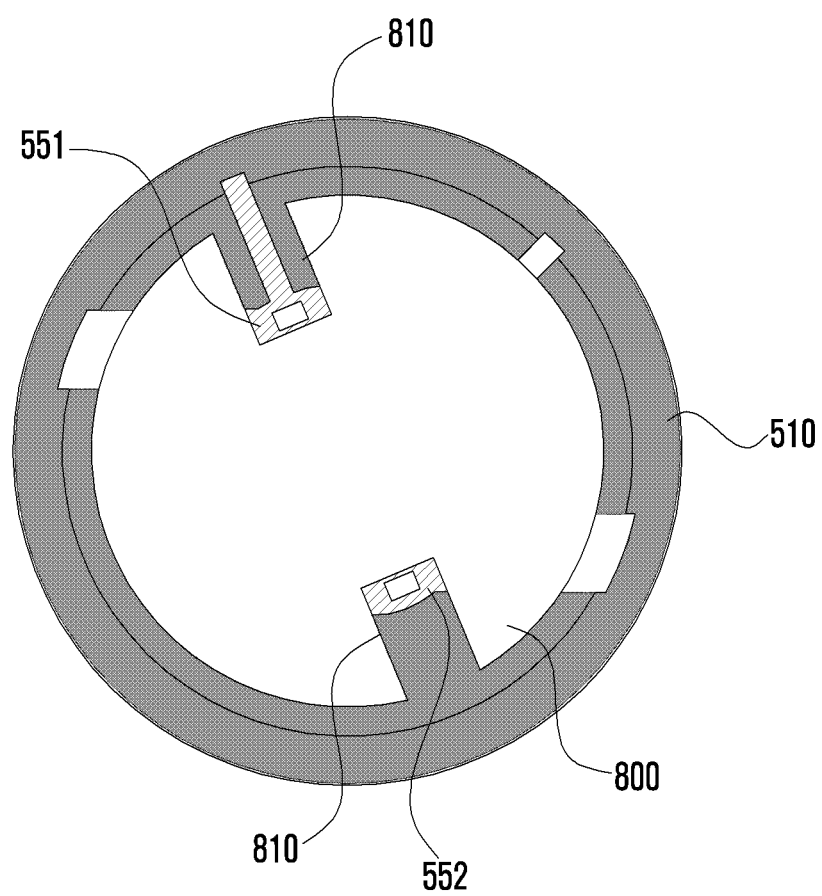
FIG. 8 is a diagram illustrating a plan view of the cover illustrated in FIG. 5 according to various embodiments.

FIG. 8 is a diagram illustrating a plan view of the cover 510 illustrated in FIG. 5 according to various embodiments.

As shown in FIG. 8, an optical film 800 may be attached to the inner surface of the cover 510. The optical film 800 may be a film having a polarization attribute. The optical film 800 may prevent and/or reduce a likelihood of a component disposed in the electronic device from being seen from the outside through the cover 510. The optical film 800 may be formed in a circular shape as a whole. The optical film 800 may have two grooves 810 extending from a portion of the outer circumference thereof to the center of the optical film 800. The first internal electrode 551 and a second internal electrode 552 disposed on the cover 510 may be exposed through the two grooves 810. Two contact units 560 may be in contact with each of the first internal electrode 551 and the second internal electrode 552 exposed through the grooves 810 of the optical film 800.

Figure 9:
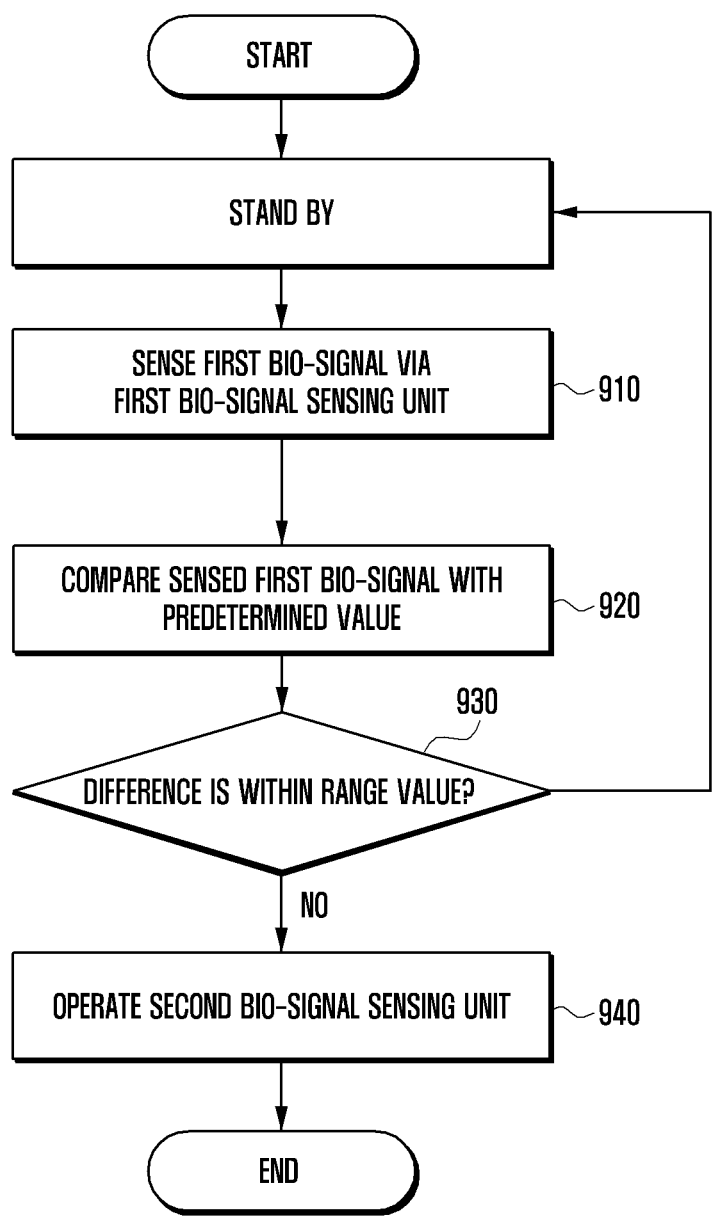
FIG. 9 is an flowchart illustrating example operations of a wearable electronic device detecting a bio-signal according to various embodiments.

FIG. 9 is an flowchart illustrating example operations of a wearable electronic device detecting a bio-signal according to various embodiments.

A processor (e.g., processor 120 in FIG. 1) of the electronic device may cause a first bio-signal sensing unit 540 to sense a first bio-signal (910).

According to various embodiments, the processor may cause the first bio-signal sensing unit 540 to sense the first bio-signal at predetermined intervals.

According to various embodiments, a user may input a command for sensing the first bio-signal through a touch input unit included in a display (e.g., display 220 in FIG. 4) of the electronic device. Here, the touch input unit may include a capacitive touch sensor or a pressure touch sensor to sense a user's touch input. The processor may cause the first bio-signal sensing unit 540 to sense the first bio-signal according to the command for sensing the first bio-signal.

According to various embodiments, a user's command for sensing the first bio-signal may be input through an external electronic device wirelessly connected to the wearable electronic device. The command input through the external electronic device for sensing the first bio-signal may be received through a communication module included in the wearable electronic device. The processor may cause the first bio-signal sensing unit 540 to sense the first bio-signal according to the command received through the communication module for sensing the first bio-signal.

The processor may cause the first bio-signal sensing unit 540 to sense the first bio-signal through various methods.

The processor may compare the first bio-signal sensed by the first bio-signal sensing unit 540 with a predetermined (e.g., specified) value (920). As described above, the first bio-signal may include a bio-signal related to a cardiac impulse of a user. The predetermined value may include information on a cardiac impulse in a normal state. Cardiac impulse information in a normal state may be different depending on personal information such as age and gender. Cardiac impulse information in a normal state may be received from a server configured to provide related information and stored. In some cases, it is possible that the first bio-signal of a user in a normal state is used as the predetermined value.

The processor checks whether a difference between the first bio-signal sensed by the first bio-signal sensing unit 540 and the predetermined value is within a range value (930). When the difference is out of the range value (930—No), the processor causes the second bio-signal sensing unit 550 to sense the second bio-signal (940). According to various embodiments, in case in which the difference between the sensed first bio-signal and the predetermined value is not within the range value, it is possible to display, on a display of the electronic device, that the sensed first bio-signal is not normal. Through this, it is possible to inform a user that the first bio-signal is out of the normal range.

As described above, the second bio-signal may include a bio-signal related to electrocardiogram. Through aforementioned operations, the user may more efficiently and accurately measure his or her health conditions.

An assembly operation of an electronic device according to various embodiments disclosed herein will be described in greater detail below with reference to FIG. 10.

Figure 10:
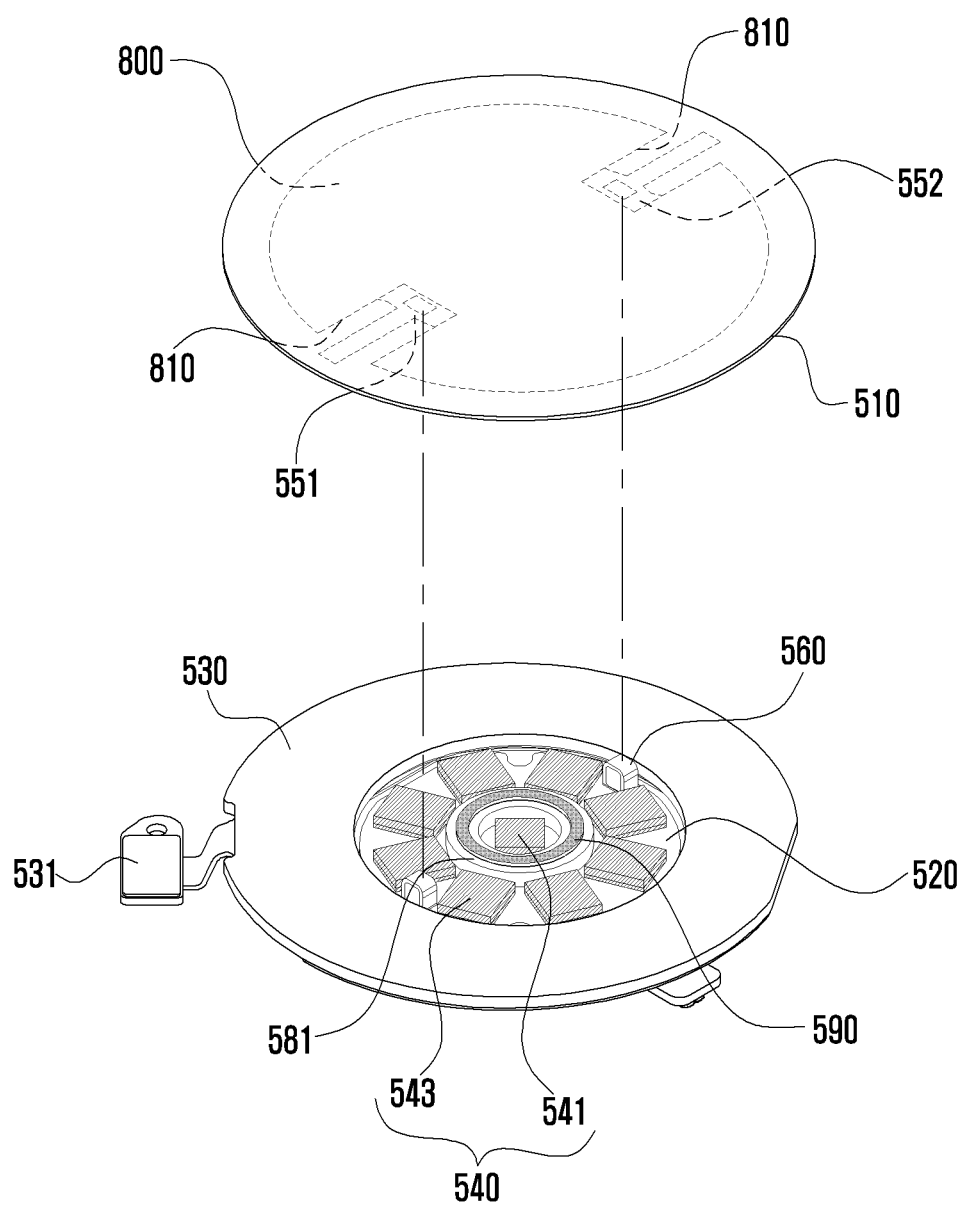
FIG. 10 is a diagram illustrating an example assembly method according to various embodiments.

FIG. 10 is a diagram illustrating an example assembly method according to various embodiments.

The wireless charging coil 530 having a ring shape may be disposed inside the cover 510. The flexible printed circuit board 520 may be disposed on the inner circumferential surface of the wireless charging coil 530. As shown in FIG. 10, the contact unit 560 mounted on the first surface of the flexible printed circuit board 520 will to be disposed in contact with the internal electrode 551 and 552 of the cover 510.

As such, in the electronic device according to various embodiments disclosed herein, the internal electrode 551 and 552 of the cover 510 may be electrically connected to the flexible printed circuit board 520 through the contact unit 560 protruding toward the first surface of the flexible printed circuit board 520. Therefore, in a state in which the internal electrode 551 and 552 of the cover 510 and the contact unit 560 of the flexible printed circuit board 520 are aligned to each other, the internal electrode 551 and 552 and the flexible printed circuit board 520 may be easily connected just by arranging the flexible printed circuit board 520 on the cover 510. As a result, it is possible to have the effect of eliminating the risk of assembly defects and reducing the assembly cost.

An electronic device, according to various example embodiments of the disclosure, may include: a display; a processor operatively connected to the display; a cover facing the display and at least a part of the cover comprises a light transmitting material; a flexible printed circuit board having a first side facing the cover, and a second side corresponding to an opposite side of the first side; a coil configured to be used for wireless charging disposed to surround the flexible printed circuit board; a first bio-signal sensing unit comprising bio-signal sensing circuitry including a light-emitting unit including light-emitting circuitry and a light-receiving unit including light-receiving circuitry mounted on the first side of the flexible printed circuit board; a second bio-signal sensing unit including an internal electrode formed inside the cover, including a portion facing the flexible printed circuit board, and an external electrode electrically connected to the internal electrode and formed outside the cover; a contact having one end mounted on the first side of the flexible printed circuit board and extending to the cover such that the opposite end of the contact is connected to the internal electrode of the second bio-signal sensing unit; and a signal processing unit mounted on the second side of the flexible printed circuit board comprising circuitry configured to process a first bio-signal sensed by the first bio-signal sensing unit and a second bio-signal sensed by the second bio-signal sensing unit.

The contact may be configured to extend in a direction perpendicular to the first surface of the flexible printed circuit board.

An inside of the contact may be filled with a buffer substance.

A first magnet disposed on the first surface of the flexible printed circuit board may be further included.

A second magnet disposed on the second surface of the flexible printed circuit board to be positioned in a space formed by the installation of the signal processing unit on the flexible printed circuit board may be further included.

The first magnet and the second magnet may be disposed so that the central axis of the first magnet is aligned with the central axis of the second magnet.

The first magnet may have a ring shape to have the light-emitting unit of the first bio-signal sensing unit disposed at the center thereof.

An optical shield may be further included between the first magnet and the cover to optically shield the first magnet and the cover such that the light-emitting unit of the first bio-signal sensing unit is optically shielded.

Multiple light-receiving units of the first bio-signal sensing unit are arranged along the outer circumference of the first magnet.

The external electrode may include a first external electrode and a second external electrode, the internal electrode of the second bio-signal sensing unit may include a first internal electrode electrically connected to the first external electrode and a second internal electrode electrically connected to the second external electrode, and two of the contact units may be provided to be connected to the first internal electrode and the second internal electrode, respectively.

The internal electrode of the second bio-signal sensing unit may extend from the outer circumference of the cover toward the center of the cover.

An optical film attached to the cover may be further included.

The optical film may be formed in a circular shape and have multiple grooves extending from a portion of the outer circumference toward the center thereof, and the first internal electrode and the second internal electrode of the internal electrode of the second bio-signal sensing unit may be arranged in the multiple grooves formed on the optical film, respectively.

The first bio-signal may include a bio-signal related to a cardiac impulse and the second bio-signal sensed by the second bio-signal sensing unit may include a bio-signal related to electrocardiogram.

The processor may be configured to control the first bio-signal sensing unit to periodically sense a first bio-signal, check a difference between the first bio-signal sensed by the first bio-signal sensing unit and a specified value, and based on the difference being out of a range value, cause the second bio-signal sensing unit to sense a second bio-signal.

The processor may be configured to check a difference between the first bio-signal sensed by the first bio-signal sensing unit and a specified value, and based on the difference being out of a range value, display, on a display of the electronic device, that the sensed first bio-signal is not normal.

The processor may be configured to: control the first bio-signal sensing unit to sense a first bio-signal, based on a touch input input through the display, check a difference between the first bio-signal sensed by the first bio-signal sensing unit and a specified value, and based on the difference being out of a range value, cause the second bio-signal sensing unit to sense a second bio-signal.

The processor may be configured to check a difference between the first bio-signal sensed by the first bio-signal sensing unit and a specified value, and based the difference being out of a range value, display, on a display of the electronic device, that the sensed first bio-signal is not normal.

The electronic device may further include a communication module comprising communication circuitry configured to perform communication with an external electronic device, the processor may be configured to: control the first bio-signal sensing unit to sense a first bio-signal, based on a request, for sensing a first bio-signal, received by the communication module from an external electronic device, check a difference between the first bio-signal sensed by the first bio-signal sensing unit and a specified value, and based on the difference being out of a range value, cause the second bio-signal sensing unit to sense a second bio-signal.

Operations for assembling an electronic device according to various example embodiments of the disclosure may include: disposing a wireless charging coil having a ring shape on a cover; and disposing a flexible printed circuit board on an inner circumference of the wireless charging coil.

The disposing the flexible printed circuit board causes one end of a contact unit to be mounted on the flexible printed circuit board and extend to the cover to be in contact with an internal electrode formed on the cover.

While the disclosure has been illustrated and described with reference to various example embodiments, it will be understood that the various example embodiments are intended to be illustrative, not limiting. It will be further understood by those skilled in the art that various changes in form and detail may be made without departing from the true spirit and full scope of the disclosure, including the appended claims and their equivalents. It will also be understood that any of the embodiment(s) described herein may be used in conjunction with any other embodiment(s) described herein.

What is claimed is:

1. A wearable electronic device comprising:
   a display;
   at least one processor operatively connected to the display;
   a cover facing the display and comprising a light-transmitting material;
   a flexible printed circuit board having a first surface facing the cover, and a second surface corresponding to an opposite surface of the first surface;
   a wireless charging coil disposed to surround the flexible printed circuit board;
   a first bio-signal sensing unit comprising a light receiver and a light emitter mounted on the first surface of the flexible printed circuit board;
   a second bio-signal sensing unit comprising an internal electrode formed inside the cover, corresponding to a portion facing the flexible printed circuit board, and an external electrode electrically connected to the internal electrode and formed outside the cover;
   a contact having one end contacting the first surface of the flexible printed circuit board, extending to the cover so that the opposite end thereof is connected to the internal electrode of the second bio-signal sensing unit; and
   a signal processor mounted on the second surface of the flexible printed circuit board comprising circuitry configured to process a first bio-signal sensed by the first bio-signal sensing unit and a second bio-signal sensed by the second bio-signal sensing unit.

2. The wearable electronic device of claim 1, wherein the contact is configured to extend in a direction perpendicular to the first surface of the flexible printed circuit board.

3. The wearable electronic device of claim 1, further comprising a first magnet disposed on the first surface of the flexible printed circuit board.

4. The wearable electronic device of claim 3, further comprising a second magnet disposed on the second surface of the flexible printed circuit board in a space formed on the second surface of the flexible printed circuit board by mounting of the signal processor.

5. The wearable electronic device of claim 4, wherein the first magnet and the second magnet are disposed so that a central axis of the first magnet is aligned with a central axis of the second magnet.

6. The wearable electronic device of claim 3, wherein the first magnet has a ring shape and the light emitter of the first bio-signal sensing unit is disposed at a center of the first magnet.

7. The wearable electronic device of claim 3, further comprising an optical shield disposed between the first magnet and the cover, wherein the light emitter of the first bio-signal sensing unit is optically shielded by the optical shield.

8. The wearable electronic device of claim 3, wherein multiple light receivers of the first bio-signal sensing unit are arranged along an outer circumference of the first magnet.

9. The wearable electronic device of claim 1, wherein the external electrode of the second bio-signal sensing unit comprises a first external electrode and a second external electrode,
wherein the internal electrode of the second bio-signal sensing unit comprises a first internal electrode electrically connected to the first external electrode and a second internal electrode electrically connected to the second external electrode, and
wherein two contacts are connected to the first internal electrode and the second internal electrode, respectively.

10. The wearable electronic device of claim 9, further comprising an optical film attached to the cover.

11. The wearable electronic device of claim 10, wherein the optical film has a circular shape and includes multiple grooves extending from a portion of an outer circumference toward a center of the optical film, and
wherein the first internal electrode and the second internal electrode of the internal electrode of the second bio-signal sensing unit are arranged in the multiple grooves formed on the optical film, respectively.

12. The wearable electronic device of claim 1, wherein the internal electrode of the second bio-signal sensing unit extends from an outer circumference of the cover toward a center of the cover.

13. The wearable electronic device of claim 1, wherein the at least one processor is configured to:
control the first bio-signal sensing unit to periodically sense a first bio-signal,
check a difference between the first bio-signal and a specified value, and
based on the difference being out of a range value, cause the second bio-signal sensing unit to sense a second bio-signal.

14. The wearable electronic device of claim 13, wherein the at least one processor is configured to:
check a difference between the first bio-signal and a specified value, and
based on the difference being out of a range value, display, on the display, that the sensed first bio-signal is not normal.

15. The wearable electronic device of claim 1, wherein the at least one processor is configured to:
control the first bio-signal sensing unit to sense a first bio-signal, based on a touch input input through the display,
check a difference between the first bio-signal and a specified value, and
based on the difference being out of a range value, cause the second bio-signal sensing unit to sense a second bio-signal.

16. The wearable electronic device of claim 15, wherein the at least one processor is configured to:
check a difference between the first bio-signal and a specified value, and
based on the difference being out of a range value, display, on the display, that the sensed first bio-signal is not normal.

17. The wearable electronic device of claim 1, further comprising a communication circuit configured to perform communication with an external electronic device,
wherein the at least one processor is configured to:
control the first bio-signal sensing unit to sense a first bio-signal, based on a request for sensing a first bio-signal, received by the communication circuit from the external electronic device,
check a difference between the first bio-signal and a specified value, and
based on the difference being out of a range value, cause the second bio-signal sensing unit to sense a second bio-signal.

18. The wearable electronic device of claim 1, wherein an inside of the contact is filled with a buffer substance.

19. The wearable electronic device of claim 1, wherein a first bio-signal sensed by the first bio-signal sensing unit includes a bio-signal related to a cardiac impulse,
wherein a second bio-signal sensed by the second bio-signal sensing unit includes a bio-signal related to electrocardiogram.

20. A method for assembling a wearable electronic device, the method comprising:
disposing a wireless charging coil having a ring shape on a cover; and
disposing a flexible printed circuit board on an inner circumference of the wireless charging coil,
wherein in the disposing of the flexible printed circuit board, a contact is brought into contact with an internal electrode formed on the cover such that the contact extends to the cover with one end of the contact contacting the flexible printed circuit board.

* * * * *